(12) United States Patent
Horton et al.

(10) Patent No.: US 10,876,938 B2
(45) Date of Patent: Dec. 29, 2020

(54) SOLID SUPPORT AND METHOD OF ENHANCING THE RECOVERY OF BIOLOGICAL MATERIAL THEREFROM

(75) Inventors: Jeffrey Kenneth Horton, Cardiff (GB); Peter James Tatnell, Cardiff (GB); Simon Laurence John Stubbs, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 0 days.

(21) Appl. No.: 13/985,089

(22) PCT Filed: Feb. 24, 2012

(86) PCT No.: PCT/EP2012/053163
§ 371 (c)(1),
(2), (4) Date: Aug. 13, 2013

(87) PCT Pub. No.: WO2012/113906
PCT Pub. Date: Aug. 30, 2012

(65) Prior Publication Data
US 2013/0330750 A1 Dec. 12, 2013

(30) Foreign Application Priority Data
Feb. 25, 2011 (GB) .................................. 1103258.8

(51) Int. Cl.
*G01N 1/36* (2006.01)
*G01N 33/543* (2006.01)
*G01N 33/544* (2006.01)

(52) U.S. Cl.
CPC ............ *G01N 1/36* (2013.01); *G01N 33/544* (2013.01); *G01N 33/54393* (2013.01); *G01N 2800/04* (2013.01); *G01N 2800/385* (2013.01)

(58) Field of Classification Search
CPC ... G01N 1/36; G01N 33/54393; G01N 33/544
See application file for complete search history.

(56) References Cited

U.S. PATENT DOCUMENTS

| | | | |
|---|---|---|---|
| 2,849,334 A | 8/1958 | Hart | |
| 3,227,075 A | 1/1966 | Guastella et al. | |
| 5,188,938 A * | 2/1993 | Khanna | G01N 33/542 422/400 |
| 5,804,684 A * | 9/1998 | Su | B01L 3/502753 422/527 |
| 5,976,572 A | 11/1999 | Burgoyne | |
| 5,985,327 A | 11/1999 | Burgoyne | |
| 6,132,971 A * | 10/2000 | Thorp | B82Y 15/00 435/6.13 |
| 6,187,540 B1 * | 2/2001 | Staub | C12Q 1/6806 206/1.5 |
| 6,645,717 B1 | 11/2003 | Smith et al. | |
| 7,670,768 B1 * | 3/2010 | Heath | C12N 15/1003 435/174 |
| 2003/0215358 A1 | 11/2003 | Schulman | |
| 2004/0112237 A1 | 6/2004 | Chaug et al. | |
| 2005/0112034 A1 * | 5/2005 | McCormick | G01N 1/31 422/536 |
| 2006/0246598 A1 * | 11/2006 | Dai et al. | 436/169 |
| 2011/0059441 A1 * | 3/2011 | Pelton | D21H 21/14 435/6.16 |

FOREIGN PATENT DOCUMENTS

| | | |
|---|---|---|
| JP | S53-19092 A | 2/1978 |
| JP | H01-291164 A | 11/1989 |
| JP | H10-179722 A | 7/1998 |
| WO | WO 96/24062 | 8/1996 |
| WO | WO 2003/020924 | 3/2003 |
| WO | WO 2005/095653 | 10/2005 |
| WO | WO 2007/056338 | 5/2007 |

OTHER PUBLICATIONS

Goodhousekeeping.com, Stain Buster—Blood, 2007, accessed May 25, 2015.*
Editors of Consumer Guide ("How to Remove Milk and Cream Stains", published Mar. 23, 2006. HowStuffWorks.com, accessed May 25, 2015.*
Dictionary.com (tissue, accessed May 25, 2015).*
Senese (General Chemistry Online, What is Cellulose? <http://antoine.frostburg.edu/chem/senese/101/consumer/faq/what-is-cellulose.shtml>, Accessed Jun. 1, 2015).*
Lloyd et al. (Pediatrics, vol. 103, No. 1, p. 1-6, 1999).*
Hewitt et al. "Tissue Handling and Specimen Preparation in Surgical Pathology" (2008) Arch Path Lab Med, vol. 132: 1929-1935.*
Mandal et al. "Methods of Rapid Detection of Foodborne Pathogens: An Overview" 2011 American Journal of Food Technology, vol. 6: 87-102.*
Harvey, M., et al., Clinical Chemistry, vol. 41, No. S6, part 2, p. S108, 1995.
Desai, N., et al., Biomaterials, vol. 12, No. 2, pp. 144-153, 1991.
Johnson, D., et al., Gene Analysis Techniques, vol. 1, No. 1, pp. 3-8, 1984.
http://www.whatman.com/DMPK.aspx and FTA DMPK Card Selection.
JP Office Action for JP Application No. 2013-554907 dated Dec. 22, 2015 (2 pages).
JP Office Action for JP Application No. 2013-554907 dated Jul. 19, 2016 (1 page).

* cited by examiner

*Primary Examiner* — Teresa E Knight
(74) *Attorney, Agent, or Firm* — Eversheds Sutherland (US) LLP

(57) ABSTRACT

The present invention relates to solid supports that are used for the storage and further processing of biological materials. The invention is particularly concerned with solid supports which have at least one surface coated with a chemical that enhances the recovery of the biological material from the support. Methods of preparing and using the solid supports are also described.

14 Claims, 3 Drawing Sheets

SOLID SUPPORT AND METHOD OF ENHANCING THE RECOVERY OF BIOLOGICAL MATERIAL THEREFROM

CROSS- REFERENCE TO RELATED APPLICATIONS

This application is a filing under 35 U.S.C. 371 of international application number PCT/EP2012/053163, filed Feb. 24, 2012, published on Aug. 30, 2012 as WO 2012/113906, which claims priority to patent application number 1103258.8 filed in Great Britain on Feb. 25, 2011.

FIELD OF THE INVENTION

The present invention relates to solid supports and is particularly concerned with solid supports which can be used in the storage, recovery and further processing of biological materials such as biopharmaceutical drugs.

BACKGROUND TO THE INVENTION

The use of solid supports such as filter paper for the collection and analysis of human blood dates back to the early 1960s, when Dr. Robert Guthrie used dried blood spot (DBS) specimens to measure phenylalanine in newborns for the detection of phenylketonuria (Mei, J., et al., 2001; Journal of Nutrition, 131:1631S-1636S). This novel application for collecting blood led to the population screening of newborns for the detection of treatable, inherited metabolic diseases. DBS have now been used for over 40 years to screen for a large range of neonatal metabolic disorders.

DBS specimens are collected by spotting whole blood onto a solid support, such as a membrane, glass fiber or paper, either from venous blood or directly from a finger or heel prick, making this method particularly suitable for the shipment of specimens from peripheral clinics to central laboratories. Furthermore, DBS packed in zip-lock plastic bags with desiccant can be stored and shipped at ambient temperature, thus avoiding the need for i) cold chain storage and ii) fast specialized transportation. DBS collected by applying a drop of blood onto an absorbent material such as Whatman 903 Neonatal STD paper are not subject to the IATA Dangerous Goods Regulations (Addendum II, Mar 2005).

Additional solid paper supports that are used for collecting, transportation and storing DBS and other bodily fluids for newborn and neonatal screening purposes include—
1. Ahlstrom 226
2. Munktell TFN (CE marked)
3. Toyo Roshi grade 545 Advantec Toyo, Tokyo (see Elvers L et al 2007; J. Inherit Medtab Dis 30, 4, 609).

All of these papers like the Whatman 903 Neonatal STD paper consist of cotton linters. The Whatman 903 Neonatal STD and Ahlstrom 226 papers are classified as Class II Medical devices. Solid paper supports that have the potential to be developed into devices for newborn and neonatal screening purposes include those manufactured by Macherey Nagel (e.g. MN818), Reeve Angel (e.g. Double ring) and Hahnemuhle Grade 2292.

The consumable costs for DBS are less than US$1 per test, and transport costs are markedly reduced compared with plasma, which requires a liquid format and specialized transportation conditions (Johannessen, A., et al., 2009; J Antimicrobial Chemotherapy, 64, 1126-1129). Although the actual assay costs remain unchanged, and the extraction of analytes from DBS involves some extra hands-on time at a centralised laboratory, the use of DBS and specifically solid paper supports is increasingly used in the storage and/or analysis of biological materials such as nucleic acids, proteins etc. In addition, DBS have also been utilised during the drug discovery process in which candidate low molecular weight drug compounds have been introduced into test animals and concentration levels in the blood monitored.

In recent years, biotechnologically-derived recombinant proteins, peptides and antibody-based drugs, as well as antisense oligonucleotides and DNA for gene therapy, have developed into mainstream therapeutic agents and now constitute a substantial portion of the compounds under clinical development. These agents are commonly termed "biotech-drugs" or "biopharmaceutical drugs" to differentiate them from low molecular weight drug compounds.

Drug Metabolism and Pharmacokinetic (DMPK) analysis of Biotech-drugs and low molecular weight drug compounds is important as DMPK analysis is vital to drug discovery as it provides insight into how drug candidates may be absorbed, metabolised and excreted by the body. Analyses are routinely performed at the drug discovery stage and involve dosing animals with the compound of interest, and measuring the drug (or metabolite) concentration in biological fluids as a function of time. This generates valuable information such as drug clearance, bioavailability etc, but demands a significant amount of time and resource (Beaudette, P., et al., 2004; J. of Chromatography B 809, 153-158).

Major problems associated with the DMPK analysis, typically conducted in drug screening programmes, are the apparent lack of a suitable storage media for maintaining stability and integrity in blood samples prior to analysis. Current methodologies use plasma or whole blood collected from the dosed animals at designated times. However, this method has a number of drawbacks including the involvement of time-consuming procedures which create a bottleneck in the analysis process. In addition, the multiple bleeding of individual animals for time-course experiments is restrictive. This puts a limitation on throughput and increases the use of animals, which has the result that fewer lead compounds can be advanced.

The small blood volume needed for DBS enables serial blood sampling from one animal rather than composite bleeds from several animals which significantly improves the quality of DMPK and toxicokinetic data and assessments. The ethical benefits of the reduced blood volume (typically 15-20 µl per spot) needed for DBS with regard to the "3Rs" (reduction, refinement, and replacement) are obvious in preclinical drug development. The numbers of test animals can be significantly reduced. In addition, non-terminal blood sampling is possible in juvenile toxicity studies which are increasingly required by authorities as part of the safety evaluation of drugs for paediatric use. Another advantage for regulatory animal toxicology studies is the increase in data quality.

Therefore due to the growing need for rapid analysis of large quantities of blood samples in pharmacokinetic research, DBS have become an attractive option. For paper to perform as a solid support for DBS it is desirable that the paper combines satisfactory mechanical properties with an ability to hold the biological material of interest in a stable condition in such a way that it can be subjected to further processing and/or analysis post-storage. Examples of such papers used for DMPK analyses are those known as 903 Neonatal specimen collection papers and also papers known as FTA and FTA Elute described, for example, in U.S. Pat. Nos. 5,75,126 and 5,939,259.

Additional solid paper supports used for DMPK analyses include the following—

1. Ahlstrom grade 226 paper:
Use of Dried Plasma Spots in the Determination of Pharmacokinetics in Clinical Studies: Validation of a Quantitative Bioanalytical Method.
Barfield, M., et al., (2011), Anal., Chem., 83, 118-124.

2. Standardized Filter paper:
Drug monitoring of lamotrigine and oxcarbazepine combination during pregnancy
Wegner, I., et al., (2010), Epilepsia, 51, 2500-2502.

3. Whatman 903, FTA (DMPK-A) and FTA Elute (DMPK-B) substrates:
Effect of storage conditions on the weight and appearance of dried blood spot samples on various cellulose-based substrates.
Denniff, P., et al., (2010), Bioanalysis, 2, 11, 1817-22.

4. Whatman DMPK-A, -B, -C:
Application of DBS for quantitative assessment of the peptide Exendin-4; comparison of plasma and DBS method by UHPLC-MS/MS.
Kehler, R., et al., (2010), Bioanalysis, 2, 8, 1461-1468.

5. Ahlstrom grade 237 paper:
Application of a Liquid Extraction Based Sealing Surface Sampling Probe for Mass Spectrometric Analysis of DBS & Mouse Whole-Body Thin Tissue Sections
Van Berkel, G., et al., (2009), Anal., Chem., 2009, 81, 21, 9146-9152.

6. Whatman FTA blood spot cards:
Dried blood spots as a sample collection technique for the determination of pharmacokinetics in clinical studies: considerations for the validation of a quantitative bioanalytical method.
Spooner, N., et al., (2009), Anal Chem. 81, 1557-63.

7. Whatman FTA Elute Micro card:
Study of dried blood spots technique for the determination of dextromethorphan and its metabolite dextrorphan in human whole blood by LC-MS/MS.
Liang, X., et al., (2009), J. Chrom B, Anal. Tech Biomed & Life Sci, 877, 799-806.

8. Whatman filter paper cards:
A liquid chromatography/Tandem mass spectrometry method for determination of 25-hydroxy vitamin D2 and 25-hydroxy vitamin D3 in dried blood spots: a potential adjunct to diabetes and cardiometabolic risk screening.
Newman, M., et al., (2009), J Diabetes Sci and Tech. 3, 156-162.

9. Toyo Roshi No. 545 filter paper (Advantec Toyo, Tokyo):
Simultaneous determination of 17α-hydroxypregnenolone and 17α-hydroxyprogesterone in DBS from low birth weight infants using LC-MS/MS.
Higashi, T., et al., (2008), J. Pharm and Biomedical Analysis, 48, 1, 177-182.

10. Whatman specimen collection paper BFC 180:
Determination of morphine & 6-acetylmorphine in blood with use of dried blood spots.
Garcia-Boy, R., et al., (2008), Therapeutic Drug Monitoring, 30, 6, 733-739.

11. Whatman filter paper (catalog no. 10535097):
Quantification of cationic anti-malaria agent methylene blue in different human biological matrices using cation exchange chromatography coupled to tandem mass spectrometry.
Burhenne, J., et al., (2008), J. Chrom B, Anal. Tech Biomed & Life Sci, 863, 273-282.

12. Whatman 3MM:
Use of filter paper for sample collection and transport in steroid pharmacology.
Howe, C., et al., (1997), Clin Chem. 43, 1408-15.

13. Whatman FTA, FTA Elute, DMPK-A, B, C, Ahlstrom 226—
Determination of Tamiflu® and active metabolite in dried blood spots using the SCAPTM DBS system and column-switching LC-MS/MS.
Heinig, K., et al., F. Hoffmann-La Roche, Basel, Switzerland.
(see: http://www.presearch.co.uk/pages/products applications/1725/Determination%20of%20Tamiflu%C2%A E%20and%20active%20metabolite%20in%20dried% 20blood%20spots%20using%20the%20SCAPTM%20 DBS%20system.pdf)

Solid paper supports that have the potential to be developed into devices for DMPK purposes include Munktell TFN grade, Toyo Roshi grade 545, Macherey Nagel (e.g. MN818), Reeve Angel (e.g. Double ring) and Hahnemuhle Grade 2292).

For effective downstream processing and analysis, the analyte of interest (such as endogenous proteins or Biotech drugs) must be easy to extract from the solid paper support using relatively simple techniques that are amenable to high throughput.

The combination of DBS and the detection of endogenous protein has been described in the scientific literature. For example, the biomarker for cystic fibrosis (CF) immunoreactive trypsin (IT), the first reported use of endogenous IT from DBS for CF screening was published by Ryley et al., in 1981 (J. Clin. Pathol. 34, 906-910). Since then, IT has been routinely used as an indicator of CF using DBS from neonates. A number of commercial organisations supply FDA approved immunoassay kits for this application. Many simply use a "paper-in" approach, in which a paper punch containing the DBS is applied directly in to the immunoassay and the analyte of interest is extracted in situ. Recently (Lindau-Shepard & Pass, 2010, Clinical Chem. 56, 445-450) demonstrated that IT exists in two different isoforms. These authors reported the development of a suspension (or paper-in) array-based immunoassay for the diagnosis of CF using the two different isoforms of IT. All these protein-based studies were carried out on uncoated Guthrie cards (Whatman 903 paper).

Since the inception of anonymous human immuno-deficiency (HIV) screening, over 1.2 million DBS tests have been carried out for the serological detection of endogenous anti-HIV antibodies in the blood from expectant mothers.

These studies have proved that i) concerns about long-term storage of blood and any associated proteins of interest have proved unfounded and ii) the presence of haem in the DBS does not interfere with assay performance.

It is therefore desirable to produce solid supports which provide a simple, stable storage medium for biological materials, including i) endogenous moieties and ii) biopharmaceutical or biotech drugs, which give a high yield or recovery of the biological material on further processing. The present invention addresses these needs and provides methods that enhance the recovery levels of biological materials such as biopharmaceutical drugs from biological samples stored as DBS on solid supports, particularly solid paper supports.

DEFINITIONS

The term "biological material" as used herein shall mean any "biomolecule", "synthetically-derived biomolecule", "biopharmaceutical drug" or "cellular component" as defined below:

i) A biomolecule is any organic molecule that is produced by a living organism, including large polymeric molecules such as proteins, polysaccharides, and nucleic acids as well as small low molecular weight molecules such as primary metabolites, secondary metabolites, and natural products.
ii) A synthetically-derived biomolecule, is a "biomolecule" as defined in i) above that is generated using recombinant DNA technologies or chemically synthesised by other non-living in-vitro methods.
iii) A biopharmaceutical drug (or "biotech drug") is a biotechnologically-derived recombinant protein, peptide or antibody-based drug, or an antisense oligonucleotide, protein nucleic acid (PNA) or deoxy ribonucleic acid (DNA) for gene therapy.
iv) A cellular component is a unique, highly organized substance or substances of which cells, and thus living organisms, are composed. Examples include membranes, organelles, proteins, and nucleic acids. Whilst the majority of cellular components are located within the cell itself, some may exist in extracellular areas of an organism.

SUMMARY OF THE INVENTION

According to a first aspect of the present invention, there is provided a solid support having at least one surface coated with a chemical that enhances the recovery of a biological material from said surface, wherein the chemical is selected from the group consisting of vinyl polymer, non-ionic synthetic polymer and protein.

In one aspect, the solid support is selected from the group consisting of paper, glass microfiber and membrane.

In another aspect, the paper is a cellulose paper. Preferably the paper is a 903 Neonatal STD or a DMPK-C card.

In a further aspect, the membrane is selected from the group consisting of polyester, polyether sulfone (PES), polyamide (Nylon), polypropylene, polytetrafluoroethylene (PTFE), polycarbonate, cellulose nitrate, cellulose acetate and aluminium oxide.

In another aspect, the vinyl polymer is polyvinyl pyrrolidone (PVP).

In a further aspect, the non-ionic synthetic polymer is poly-2-ethyl-2-oxazoline (PEOX).

In one aspect, the protein is selected from the group consisting of albumin and casein.

According to a second aspect of the present invention, there is provided a method of recovering a biological material from a solid support comprising the steps of
i) contacting a surface of a solid support as hereinbefore described with a sample containing a biological material;
ii) drying the sample on the surface of the support;
iii) storing the support; and
iv) extracting the biological material from the surface.

In one aspect, step iii) comprises storing the paper support at a temperature in the range of 15 to 40° C. Preferably, the temperature is in the range of 20 to 30° C. In another aspect, the paper support is stored at a lower temperature depending on the thermal stability of the biological material.

The nature of the sample will depend upon the source of the biological material. For example, the source may be from a range of biological organisms including, but not limited to, virus, bacterium, plant and animal. Preferably, the source will be a mammalian or a human subject. For mammalian and human sources, the sample may be selected from the group consisting of tissue, cell, blood, plasma, saliva and urine.

In another aspect, the biological material is selected from the group consisting of biomolecule, synthetically- derived biomolecule, cellular component and biopharmaceutical drug.

In a further aspect, the biological material is a biopharmaceutical drug.

In one aspect, the support is a paper. Preferably the paper is a cellulose paper. More preferably, the paper is a 903 Neonatal STD or a DMPK-C card.

According to a third aspect of the present invention, there is provided a method of making a solid support as hereinbefore described, comprising coating at least one surface of a solid support with a solution of a chemical that enhances the recovery of a biological material from said surface, wherein the chemical is selected from the group consisting of vinyl polymer, non-ionic synthetic polymer and protein.

In one aspect, the chemical is selected from group consisting of polyvinyl pyrrolidone (PVP), poly-2-ethyl-2-oxazoline (PEOX), albumin and casein.

In another aspect, the solid support is a paper. Preferably the paper is a cellulose paper. More preferably, the cellulose paper is a 903 Neonatal STD or a DMPK-C card.

According to a fourth aspect of the present invention, there is provided a use of a solid support as hereinbefore described for enhancing the recovery of a biological material from a surface thereof.

In one aspect, the biological material is a biopharmaceutical drug.

DETAILED DESCRIPTION OF THE INVENTION

Recombinant IL-2±carrier (R & D Systems; Cat. 202-IL-CF-10 µg; lot AE4309112 and Cat. 202-IL-10µg; lot AE4309081 respectively) was dissolved in either Dulbecco's PBS without calcium and magnesium (PAA; Cat. H15-002, lot H00208-0673), EDTA-anti-coagulated human, rabbit or horse blood (TCS Biosciences) at 50 pg or 100 pg/µl.

Aliquots (1 µl containing 0, 50 or 100 pg of IL-2) were applied to the following GE Healthcare filter papers; 903 Neonatal STD card, Cat. 10538069, lot 6833909 W082; DMPK-A card, Cat. WB129241, lot FT6847509; DMPK-B card, Cat. WB129242, Lot FE6847609 and DMPK-C card, Cat. WB129243, Lot FE6847009. Samples were allowed to dry overnight at ambient temperature and humidity.

Punches (3 mm diameter) were extracted from each paper type using the appropriately sized Harris Uni-core punch (Sigma, Cat.Z708860-25ea, lot 3110). Single punches were placed into individual wells of the IL-2 microplate derived from the Human IL-2 Quantikine ELISA (R & D Systems, Cat. D0250, lot 273275). These plates are coated with a mouse monoclonal antibody against IL-2. The IL-2 protein was eluted from the paper punch using the assay buffer (100 µl) supplied with the Quantikine kit. All subsequent steps were performed according to the instructions supplied with the Quantikine kit using a "paper in" method (paper punches are placed directly into the assay buffer and the analyte eluted directly in situ). On completion of the assay the optical density of the microplate was monitored at 450 nm using a Thermo Electron Corporation, Multiskan Ascent. The recovery of IL-2 was determined by comparing values to a standard curve of known IL-2 concentrations. A fresh IL-2 standard curve was prepared for each individual experiment.

Additional experiments involved the addition of IL-2-spiked blood to the 903 Neonatal STD and DMPK-C cards after the cards had been saturation dipped in several chemical solutions (as described below).

Chemicals Used

A list of the chemicals and their sources is given below.
Poly-ethyl-enemine, 50% in water (Fluka; Cat. P3143, lot 29k1492).
Poly-vinyl-pyrolodine, 1% in water (Sigma; Cat.PVP40-100 mg, lot 11 pk0097).
Inulin, 1% in water (Sigma; Cat. 12255-100 g, lot 079F7110).
Poly-2-ethyl-2-oxazoline, 1% in water (Aldrich Cat. 372846, lot 30498PJ).
Albumin, 1% in water (Sigma, Cat A2153-10 g, lot 049k1586).
Caesin from bovine milk, 1% in water (Sigma, Cat. C5890-500 g, lot 089k0179).
Poly-ethylene glycol 1000, 1% in water (Biochemika, Cat. 81189, lot 1198969).
Poly-ethylene glycol 200, 1% in water (Fluka, Cat. 81150, lot 1384550).

Experimental Results

Figure 1:
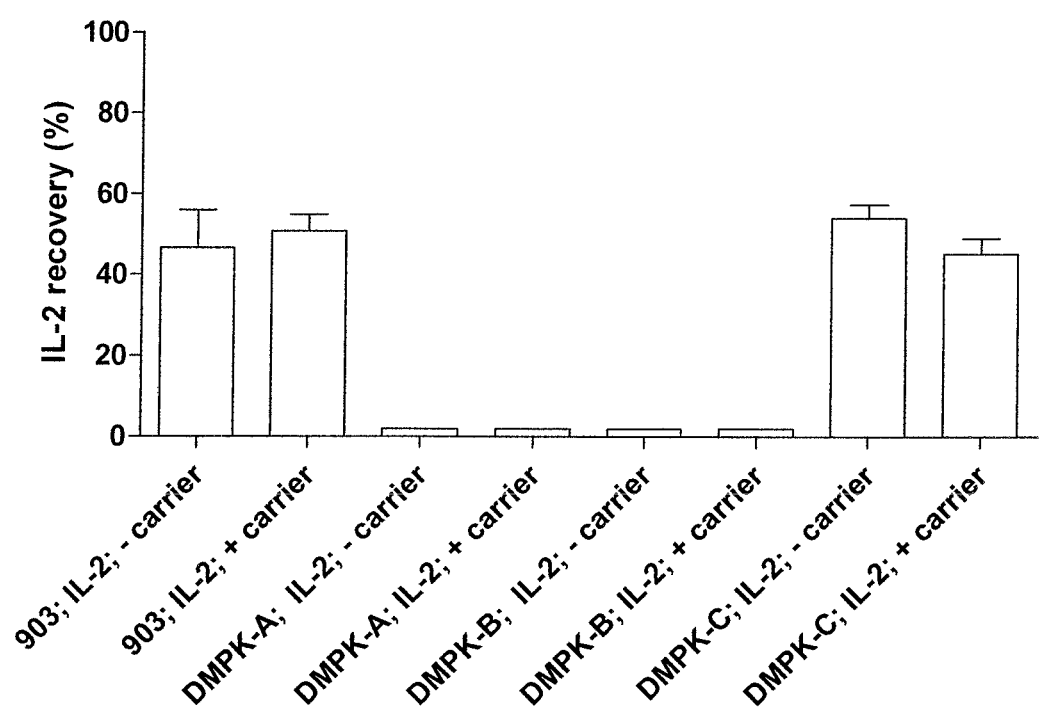
FIG. 1 presents the recovery of exogenously-added IL-2 from dried blood spots applied to various paper matrices.

When IL-2 was dissolved in EDTA-anti-coagulated blood, the 903 and DMPK-C cards facilitated the recovery of 45-55% of the cytokine, while only 2-3% was recovered from the DMPK-A and B cards (see Table 1 and FIG. 1). The 903 and DMPK-C cards are the basic base papers and have not been dipped or coated with any chemical, whilst the DMPK-A and B cards are coated with a proprietary mixture of chemicals that facilitate the denaturation and inactivation of proteins, micro-organisms and cells respectively. These cards have been designed to facilitate the transportation and prolonged storage of nucleic acids. Therefore the low IL-2 recovery levels observed when using the DMPK-A and B cards may actually be a reflection of the presence of these denaturing reagents and the ELISA-based antibody detection system used. The ELISA detection system requires the eluted IL-2 to exhibit an intact native structure.

TABLE 1

The Recovery of exogenously-added IL-2 from dried blood spots applied to various paper types. The p-value compares ± carrier for each paper type. The presence of the carrier had no significant effect on the recovery of IL-2 (p-value > 0.05).

| Paper type | IL-2 recovery (%) | p-value |
| --- | --- | --- |
| 903; minus carrier | 46.9 ± 13.3 | >0.05 |
| 903; plus carrier | 50.7 ± 5.8 | |
| DMPK A; minus carrier | 2.0 ± 0.0 | >0.05 |
| DMPK A; plus carrier | 2.0 ± 0.0 | |
| DMPK B; minus carrier | 2.0 ± 0.0 | >0.05 |
| DMPK B; plus carrier | 2.0 ± 0.0 | |
| DMPK C; minus carrier | 53.9 ± 4.8 | >0.05 |
| DMPK C; plus carrier | 45.2 ± 5.4 | |

No IL-2 recovery was observed when the cytokine was dissolved in PBS irrespective of the paper type used (data not shown). The IL-2 recovery levels observed in the absence of added IL-2 were essentially equivalent to background levels indicating that the EDTA-anti-coagulated blood contain negligible amounts of endogenous IL-2 (data not shown).

Figure 2:
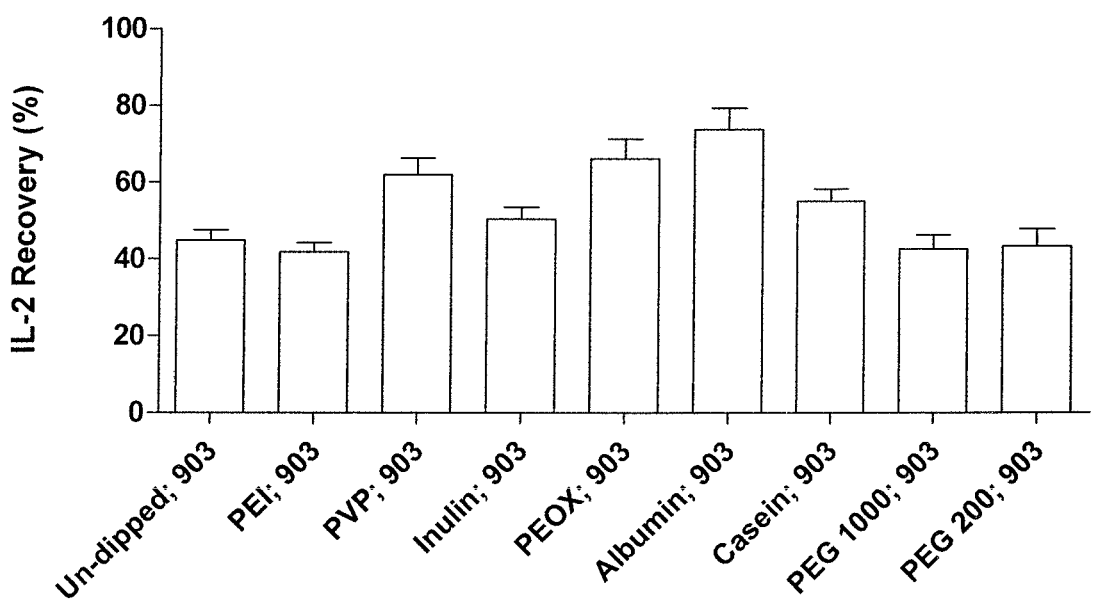
FIG. 2 presents the recovery of exogenously-added IL-2 from dried blood spots applied to 903 Neonatal STD papers coated with various chemicals.
Figure 3:
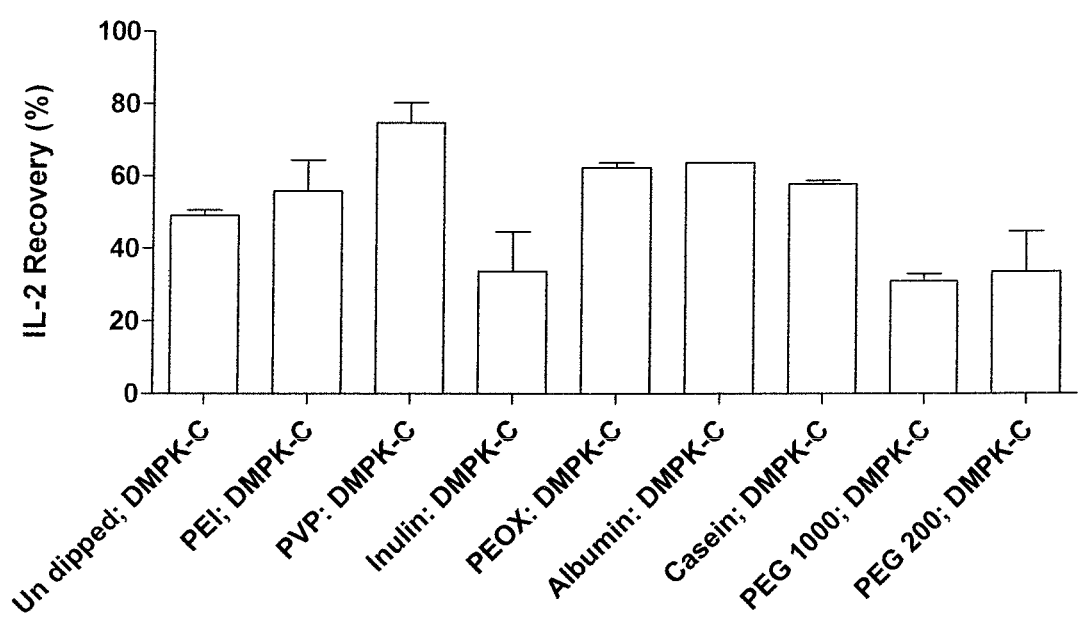
FIG. 3 presents the recovery of exogenously-added IL-2 from dried blood spots applied to DMPK-C papers coated with various chemicals.

Several chemicals were used to saturation dip the 903 Neonatal STD and DMPK-C cards, some of which appeared to facilitate the recovery of elevated IL-2 levels compared to non-dipped papers (p-value<0.05). For both the 903 Neonatal STD and DMPK-C cards (Tables 2 and 3; FIGS. 2 and 3), chemicals such as poly-vinyl-pyrolodine, poly-2-ethyl-2-oxazoline, albumin and casein facilitated a significant increase in IL-2 recovery levels (mean>55% compared to ~45% observed for the corresponding un-dipped paper).

TABLE 2

The Recovery of exogenously-added IL-2 from dried blood spots applied to 903 Neonatal STD papers coated with various chemicals. The table is derived from 2 independent experiments (n = 6). The p-value compares the values derived from the dipped papers to those derived from the Un-dipped 903 paper.

| Chemical | IL-2 recovery (%) | p-value |
| --- | --- | --- |
| Un-dipped | 44.9 ± 6.5 | n/a |
| Poly-ethyl-enemine (PEI) | 41.8 ± 6.0 | >0.05 |
| Poly-vinyl-pyrolodine (PVP) | 62.0 ± 10.7 | <0.05 |
| Inulin | 50.4 ± 7.6 | >0.05 |
| Poly-2-ethyl-2-oxazoline (PeOX) | 66.1 ± 12.6 | <0.05 |
| Albumin | 73.8 ± 13.6 | <0.05 |
| Caesin | 55.0 ± 7.8 | <0.05 |
| Poly-ethylene glycol 1000 (PEG 1000) | 42.5 ± 9.1 | >0.05 |
| Poly-ethylene glycol 200 (PEG 200) | 43.3 ± 11.0 | >0.05 |

TABLE 3

The Recovery of exogenously-added IL-2 from dried blood spots applied to DMPK-C coated with various chemicals (n = 3). The p-value compares the values derived from the dipped papers to those derived from the Un-dipped DMPK-C paper. Albumin* n = 1.

| Chemical | IL-2 recovery (%) | p-value |
| --- | --- | --- |
| Un-dipped | 49.0 ± 2.1 | n/a |
| Poly-ethyl-enemine (PEI) | 55.8 ± 12.2 | >0.05 |
| Poly-vinyl-pyrolodine (PVP) | 74.7 ± 7.8 | <0.05 |
| Inulin | 33.6 ± 15.4 | >0.05 |
| Poly-2-ethyl-2-oxazoline (PeOX) | 62.2 ± 2.0 | <0.05 |
| Albumin* | 63.7 | increase |
| Caesin | 57.7 ± 1.5 | <0.05 |
| Poly-ethylene glycol 1000 (PEG 1000) | 31.0 ± 2.8 | >0.05 |
| Poly-ethylene glycol 200 (PEG 200) | 33.5 ± 15.7 | >0.05 |

While preferred illustrative embodiments of the present invention are described, one skilled in the art will appreciate that the present invention can be practised by other than the described embodiments, which are presented for the purposes of illustration only and not by way of limitation. The present invention is limited only by the claims that follow.

The invention claimed is:
1. A method of recovering a biological material from a solid support comprising the steps of:
   i) providing the solid support having a surface coated with a chemical selected from the group consisting of poly-vinyl pyrrolidone (PVP), poly-2-ethyl-2-oxazoline (PEOX), and casein; then
   ii) applying a sample containing the biological material to be in direct contact with the surface of the solid support and to form a sample spot, wherein the sample is selected from the group consisting of cell, blood, plasma, saliva, and urine; then iii) drying the sample spot to form a dried sample spot on the surface of the solid support; then iv) storing the dried sample spot; and then v) extracting the biological material from the dried sample spot from the surface of the solid support, wherein the solid support is a paper.

2. The method of claim 1, wherein the paper is a cellulose paper.

3. The method of claim 1, wherein step iv) comprises storing the solid support at a temperature in the range of 15 to 40° C.

4. The method of claim 1, wherein the biological material is selected from the group consisting of biomolecule, synthetically-derived biomolecule, cellular component and biopharmaceutical drug.

5. The method of claim 1, wherein the biological material is a biopharmaceutical drug.

6. The method of claim 1, wherein the sample is blood and the dried sample spot is a dried blood spot.

7. The method of claim 1, wherein the providing step further comprises saturation dipping of the solid support in a solution comprising the chemical.

8. A method of recovering a biological material from a solid support comprising the steps of:
   i) providing the solid support having a surface coated with a chemical selected from the group consisting of polyvinyl pyrrolidone (PVP), poly-2-ethyl-2-oxazoline (PEOX), and casein; then
   ii) applying a sample containing the biological material to be in direct contact with the surface of the solid support and to form a sample spot, wherein the sample is selected from the group consisting of cell, blood, plasma, saliva, and urine; then
   iii) drying the sample spot on the surface of the solid support; then
   iv) storing the dried sample spot; and then
   v) extracting the biological material from the dried sample spot from the surface of the solid support,
   wherein the biological material is a biopharmaceutical drug.

9. The method of claim 8, wherein the solid support is selected from the group consisting of paper, glass microfiber and membrane.

10. The method of claim 9, wherein the paper is a cellulose paper.

11. The method of claim 9, wherein the membrane is selected from the group consisting of polyester, polyether sulfone (PES), polyamide (Nylon), polypropylene, polytetrafluoroethylene (PTFE), polycarbonate, cellulose nitrate, cellulose acetate and aluminium oxide.

12. The method of claim 9, wherein step iv) comprises storing the solid support at a temperature in the range of 15 to 40° C.

13. A method of recovering a biological material from a solid support comprising the steps of:
   i) providing the solid support having a surface coated with a chemical selected from the group consisting of polyvinyl pyrrolidone (PVP), poly-2-ethyl-2-oxazoline (PEOX) and casein; then
   ii) applying a sample containing the biological material to be in direct contact with the surface of the solid support and to form a sample spot, wherein the sample is selected from the group consisting of cell, blood, plasma, saliva, and urine; then
   iii) drying the sample spot to form a dried sample spot on the surface of the solid support; then
   iv) storing the dried sample spot; and then
   v) extracting the biological material from the dried sample spot from the surface of the solid support, wherein the solid support is selected from the group consisting of paper, glass microfiber and membrane, and wherein the membrane is selected from the group consisting of polyester, polyether sulfone (PES), polypropylene, polytetrafluoroethylene (PTFE), polycarbonate, cellulose nitrate, cellulose acetate and aluminium oxide.

14. The method of claim 13, wherein the biological material is selected from the group consisting of biomolecule, synthetically-derived biomolecule, cellular component and biopharmaceutical drug.

* * * * *